United States Patent
Takahashi

(10) Patent No.: US 9,156,753 B2
(45) Date of Patent: Oct. 13, 2015

(54) METHOD FOR REMOVING MOISTURE FROM FLUORINE-CONTAINING COMPOUNDS

(75) Inventor: Kazuhiro Takahashi, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 13/819,910

(22) PCT Filed: Sep. 6, 2011

(86) PCT No.: PCT/JP2011/070253
§ 371 (c)(1),
(2), (4) Date: Feb. 28, 2013

(87) PCT Pub. No.: WO2012/033088
PCT Pub. Date: Mar. 15, 2012

(65) Prior Publication Data
US 2013/0158305 A1    Jun. 20, 2013

(30) Foreign Application Priority Data

Sep. 7, 2010   (JP) ................................. 2010-200218

(51) Int. Cl.
*C07C 17/38*  (2006.01)
*C07C 17/389* (2006.01)
(Continued)

(52) U.S. Cl.
CPC .............. *C07C 17/38* (2013.01); *B01D 53/263* (2013.01); *B01D 53/28* (2013.01); *B01D 2251/302* (2013.01); *B01D 2251/402* (2013.01); *B01D 2251/404* (2013.01); *B01D 2251/60* (2013.01); *B01D 2252/10* (2013.01);

(Continued)

(58) Field of Classification Search
CPC ....................................................... C07C 17/38
USPC ........................................ 570/177, 179, 123
See application file for complete search history.

(56) References Cited

U.S. PATENT DOCUMENTS 2,877,276 A  *  3/1959  Sanders et al. ................ 570/238
5,679,875 A  *  10/1997 Aoyama et al. ............... 570/156
(Continued)

FOREIGN PATENT DOCUMENTS

JP      50-12405       5/1975
JP      50012405 B  *  5/1975
(Continued)

OTHER PUBLICATIONS

Naito, D. et al. Patent No. JP50012405B; May 12, 1975; English Abstract.*
(Continued)

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

The present invention provides a method for removing moisture from fluorine-containing compounds, the method comprising bringing a fluorine-containing compound contaminated with moisture into contact with an aqueous solution containing a metal salt. The method of the present invention can continuously and efficiently remove moisture from various fluorine-containing compounds, such as hydrofluoroolefins. In addition, the method produces less waste, etc., and is an industrially advantageous moisture removal method.

7 Claims, 1 Drawing Sheet

(51) Int. Cl.
   *C07C 21/18*   (2006.01)
   *B01D 53/26*   (2006.01)
   *B01D 53/28*   (2006.01)

(52) U.S. Cl.
   CPC ...... *B01D 2252/103* (2013.01); *B01D 2256/26* (2013.01); *B01D 2257/80* (2013.01); *C07C 17/389* (2013.01); *C07C 21/18* (2013.01)

(56) References Cited

U.S. PATENT DOCUMENTS 5,723,702 A * 3/1998 Kwon et al. ............... 570/177
6,346,172 B1 * 2/2002 Tsuda et al. ............... 203/14
6,559,096 B1 * 5/2003 Smith et al. ............... 502/411
2009/0287026 A1 * 11/2009 Kopkalli et al. ............ 570/156

FOREIGN PATENT DOCUMENTS

| JP | 2009-539598 | 11/2009 |
| WO | 2007/144632 | 12/2007 |
| WO | WO 2007144632 A1 * | 12/2007 |

OTHER PUBLICATIONS

International Search Report issued Nov. 22, 2011 in International (PCT) Application No. PCT/JP2011/070253.

* cited by examiner

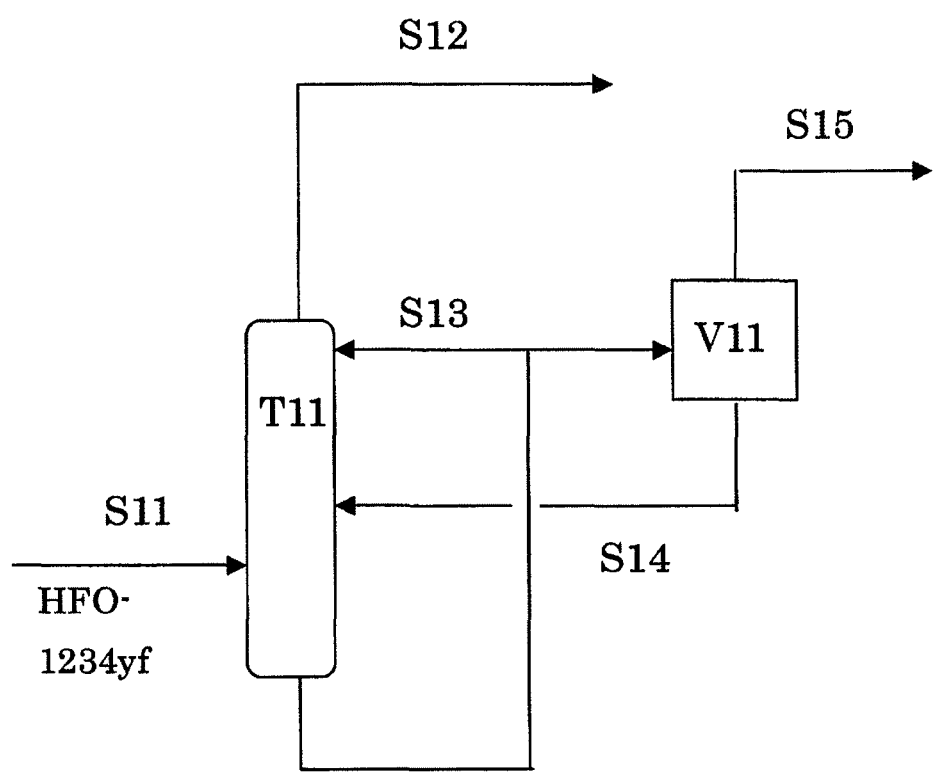

METHOD FOR REMOVING MOISTURE FROM FLUORINE-CONTAINING COMPOUNDS

TECHNICAL FIELD

The present invention relates to a method for removing moisture from fluorine-containing compounds.

BACKGROUND ART

Pentafluoroethane (HFC-125), difluoromethane (HFC-32), and other hydrofluorocarbons (HFC) are widely used as important alternatives for chlorofluorocarbons (CFC), hydrochlorofluorocarbons (HCFC), and other substances that may destroy the ozone layer. Hydrofluorocarbons have various applications, such as heat transfer media, refrigerants, foaming agents, solvents, cleaning agents, propellants, and fire extinguishers, and are consumed in large amounts.

However, these hydrofluorocarbons are potent global-warming substances. Many people are concerned that their diffusion may affect global warming. To combat this, hydrofluorocarbons are collected after being used; however, not all of them can be collected, and their diffusion due to leakage, etc., cannot be disregarded. In particular, for use in refrigerants, heat transfer media, etc., although substitution of hydrofluorocarbons with $CO_2$ or hydrocarbon-based substances has been studied, $CO_2$ refrigerants have many difficulties in reducing comprehensive greenhouse gas emissions, including energy consumption, because of the requirement of large equipment due to the low efficiency of the $CO_2$ refrigerants, and hydrocarbon-based substances have safety problems due to their high flammability.

Recently, hydrofluoroolefins with a low warming potential are attracting attention as substances that can solve these problems. "Hydrofluoroolefin" is a generic name for unsaturated hydrocarbons containing hydrogen and fluorine. Most of them are obtained by dehydrohalogenation of corresponding alkanes. For example, as a typical method for producing 2,3,3,3-tetrafluoropropene (HFO-1234yf), which is a hydrofluoroolefin, a method of eliminating HF from 1,1,1,2,3-pentafluoropropane (HFC-245eb) or 1,1,1,2,2-pentafluoropropane (HFC-245cb) is known. Since HFO-1234yf obtained by this method is in the form of a mixture with HF, it is necessary to somehow remove the HF. The simplest method of removing acid from a mixed gas of hydrofluoroolefin and acid is to absorb the acid with water. In this method, however, mist and water corresponding to vapor pressure are inevitably mixed into hydrofluoroolefins. There are various other sources of water, such as moisture contained in the starting materials, moisture produced from the catalyst, and moisture remaining in the equipment. Moisture contained in hydrofluoroolefins, which are finished products, affects their stability, device corrosiveness, refrigerant capability, etc., and is therefore one of the most important factors of quality control. The method for removing moisture is a particularly important technique.

As the method for removing moisture from hydrofluoroolefins, a method using a molecular sieve (e.g., zeolite) as a water absorbent is known. For example, Patent Literature 1 discloses a method for drying a fluid of a fluoropropene, such as HFO-1234yf, by passing it through zeolite. However, a large packed column is required to treat fluoropropenes with a low moisture content using a water absorbent, which causes poor treatment efficiency. In addition, in the method using an absorbent, there are problems that it is necessary to regularly stop the equipment to recover the performance of the absorbent and exchange the absorbent, which leads to low productivity and necessitates the use of two series of equipment. Moreover, a large amount of industrial waste is generated during the exchange of the absorbent. Furthermore, depending on the hydrofluoroolefins to be treated, they may be absorbed to the absorbent, presumably inhibiting the absorption of water that should be essentially removed.

For the above reasons, there is a demand for more efficient methods for removing moisture from various fluorine-containing compounds, such as hydrofluoroolefins.

CITED LIST

Patent Literature

PTL 1: WO 2007/144632

SUMMARY OF INVENTION

Technical Problem

The present invention was made in view of the above-described current status of the prior art. A primary object of the invention is to provide an industrially advantageous moisture removal method that can continuously and efficiently remove moisture from various fluorine-containing compounds, such as hydrofluoroolefins, and that produces less waste, etc.

Solution to Problem

The present inventor conducted extensive research to achieve the above object. As a result, the present inventor found that the moisture contaminating a fluorine-containing compound can be continuously and efficiently removed by bringing the fluorine-containing compound into contact with a high-concentration aqueous solution of metal salt. The present inventor also found that this method is economically advantageous because the aqueous solution of metal salt used in the dehydration process can be repeatedly used by reducing the moisture content thereof, and that since no waste is generated, the method has less environmental impact and is industrially excellent. Another finding was that after the moisture content of the fluorine-containing compound is reduced by this method, dehydration is carried out using a water adsorbent, such as a molecular sieve, thereby greatly reducing the moisture content of the fluorine-containing compound by a simple process, and extending the life of the water adsorbent and the period of time before having to recover the performance of the water adsorbent. The present invention has been accomplished as a result of further research based on these findings.

More specifically, the present invention provides the following method for removing moisture from fluorine-containing compounds.

Item 1. A method for removing moisture from fluorine-containing compounds, the method comprising bringing a fluorine-containing compound contaminated with moisture into contact with an aqueous solution containing a metal salt.

Item 2. The method according to Item 1, wherein the fluorine-containing compound is at least one compound selected from the group consisting of hydrofluoroolefins, hydrochlorocarbons, hydrochlorofluorocarbons, and hydrofluorocarbons.

Item 3. The method according to Item 2, wherein the fluorine-containing compound is a hydrofluoroolefin.

Item 4. The method according to Item 3, wherein the fluorine-containing compound is 2,3,3,3-tetrafluoropropene.

Item 5. The method according to any one of Items 1 to 4, wherein the metal salt is at least one member selected from the group consisting of lithium chloride, calcium chloride, magnesium chloride, and lithium bromide.

Item 6. The method according to Item 5, wherein the metal salt is lithium chloride.

Item 7. The method according to any one of Items 1 to 6, wherein the aqueous solution containing a metal salt has a concentration of 20 to 50 wt. %.

Item 8. The method according to any one of Items 1 to 7, comprising the steps of reducing the moisture content of the metal salt-containing aqueous solution used in the method according to any one of Items 1 to 7, and then reusing the aqueous solution to remove the moisture from the fluorine-containing compound.

Item 9. A method for removing moisture from fluorine-containing compounds, the method comprising the steps of removing moisture from a fluorine-containing compound by the method according to any one of Items 1 to 8, and then bringing the thus-treated fluorine-containing compound into contact with a water adsorbent.

The method for removing moisture from fluorine-containing compounds according to the present invention is described in detail below.

Target Compounds

The target compounds of the present invention are fluorine-containing compounds, the type of which is not particularly limited. In particular, when the target compounds are hydrofluoroolefins and their intermediates, such as hydrochlorocarbons, hydrochlorofluorocarbons, and hydrofluorocarbons, which may be contaminated with moisture during the production thereof, the method of the present invention is advantageous because products whose moisture content is efficiently reduced can be obtained.

Specific examples of hydrofluoroolefins to be treated by the present invention include compounds represented by the following chemical formulae:

$CF_3CF=CF_2$ (HFO-1216yc), $CF_3CF=CHF$ (HFO-1225ye), $CF_3CF=CH_2$ (HFO-1234yf), $CF_3CH=CHF$ (HFO-1234ze), $CF_3CH=CH_2$(HFO-1243zf), $CF_3CCl=CH_2$ (HCFO-1233xf), $CF_2ClCCl=CH_2$ (HCFO-1232xf), $CF_3CH=CHCl$ (HCFO-1233zd), $CF_3CCl=CHCl$ (HCFO-1223xd), $CClF_2CCl=CHCl$ (HCFO-1222xd), $CFCl_2CCl=CH_2$ (HCFO-1231xf), $CH_2ClCCl=CCl_2$ (HCO-1230xa).

Specific examples of hydrochlorocarbons include $CCl_3CHClCH_2Cl$ (HCC-240db), etc. Specific examples of hydrochlorofluorocarbons include $CCl_2FCHClCH_2Cl$ (HCFC-241db), $CClF_2CHClCH_2Cl$ (HCFC-242dc), $CF_3CHClCH_2Cl$ (HCFC-243db), $CF_3CHClCH_2F$ (HCFC-244db), $CF_3CClFCH_3$ (HCFC-244bb), etc. Specific examples of hydrofluorocarbons include $CF_3CHFCHF_2$ (HFC-236ea), $CF_3CF_2CH_3$ (HFC-245cb), $CF_3CH_2CHF_2$ (HFC-245fa), $CF_3CHFCH_2F$ (HFC-245eb), etc.

Method for Removing Moisture

In the method for removing moisture from fluorine-containing compounds according to the present invention, it is necessary to bring the target fluorine-containing compound contaminated with moisture into contact with an aqueous solution containing a metal salt. The moisture contained in the fluorine-containing compound is thereby absorbed by the metal salt-containing aqueous solution to reduce the moisture content of the fluorine-containing compound.

The method of bringing the fluorine-containing compound contaminated with moisture into contact with the metal salt-containing aqueous solution is not particularly limited. For example, when the fluorine-containing compound is in the form of a gas, the fluorine-containing compound is bubbled into the metal salt-containing aqueous solution. Alternatively, the metal salt-containing aqueous solution is directly sprayed onto the fluorine-containing compound contaminated with moisture; or the metal salt-containing aqueous solution is impregnated into a porous material, such as a ceramic or activated carbon, and the porous material is then brought into contact with the fluorine-containing compound contaminated with moisture. In particular, the moisture content of the fluorine-containing compound can be efficiently reduced by using a water absorption column, and by spraying the metal salt-containing aqueous solution from the top portion of the column, introducing the gaseous fluorine-containing compound from the bottom portion of the column, and extracting it from the top portion. In this method, the fluorine-containing compound and the metal salt-containing aqueous solution can be efficiently brought into contact with each other by filling the water absorption column with a spherical or granular material that does not react with the fluorine-containing compound or the metal salt.

The treatment temperature, treatment pressure, and other conditions of the above method using a water absorption column are not particularly limited. Conditions may be selected so that the fluorine-containing compound is present as a gas, and the moisture can be efficiently absorbed. Generally, the fluorine-containing compound may be supplied to the water absorption column at normal temperature and normal pressure while being slightly pressurized under conditions required to introduce the fluorine-containing compound into the water absorption column.

Metal salts that are usable for the metal salt-containing aqueous solution are generally those having hygroscopicity and being usable as desiccants or the like. As such metal salts, alkali metal halides, alkaline earth metal halides, etc., can be used. Examples of alkali metals include Li, Na, K, etc., and examples of alkaline earth metals include Ca, Mg, etc. Further, examples of halides include chloride, bromide, etc.

Specific examples of preferable metal salts include lithium chloride (LiCl), calcium chloride ($CaCl_2$), magnesium chloride ($MgCl_2$), lithium bromide (LiBr), etc. LiCl is particularly preferable in terms of being capable of efficiently absorbing moisture.

The concentration of the metal salt in the metal salt-containing aqueous solution is preferably as high as possible so that the metal salt-containing aqueous solution can efficiently absorb moisture. However, an overly high concentration facilitates crystallization of the metal salt. The specific concentration range may be as high as possible within a range in which the metal salt is not crystallized, depending on the type of metal salt used. For example, when LiCl is used, the concentration is generally preferably about 20 to 50 wt. %, and more preferably about 36 to 42 wt. %.

The moisture content of the fluorine-containing compound can also be reduced by using, in place of the metal salt-containing aqueous solution, a water adsorbent, such as concentrated sulfuric acid, glycerin, or triethylene glycol, or by using such a water adsorbent in combination with the metal salt-containing aqueous solution.

In the present invention, after moisture is removed from the fluorine-containing compound by the above method, the moisture content can be further reduced by performing, if necessary, dehydration using a water adsorbent, such as a molecular sieve. Thereby, high-quality fluorine-containing compounds with a lower moisture content can be easily obtained. In addition, this method can extend the life of the water adsorbent absorbent and the period of time before having to recover the performance of the water adsorbent, and enables the dehydration of fluorine-containing compounds under industrially advantageous conditions.

As the water adsorbent, known water adsorbents absorbents can be used. Examples of such water adsorbents include zeolite and other molecular sieves, silica gel, silica alumina, etc. Dehydration using a water adsorbent can be performed by a known method. For example, the fluorine-containing compound dehydrated with a metal salt-containing aqueous solution is supplied to a dehydrator filled with a water adsorbent, and passed through the dehydrator.

Advantageous Effects of Invention

According to the method of the present invention for removing moisture from fluorine-containing compounds, the moisture content of various fluorine-containing compounds (e.g., hydrofluoroolefins) contaminated with moisture can be reduced continuously and efficiently by a simple process. Moreover, the method of the present invention is economically advantageous because the aqueous solution of metal salt used in the dehydration process can be repeatedly used by reducing the moisture content thereof. Furthermore, the method of the present invention has less environmental impact because no waste is generated, and the moisture content of fluorine-containing compounds can be reduced under industrially advantageous conditions.

BRIEF DESCRIPTION OF DRAWING

FIG. 1 is a flow diagram showing the dehydration process of HFO-1234yf in Example 1.

DESCRIPTION OF EMBODIMENT

The present invention is described in more detail below with reference to an Example. However, the present invention is not limited to the Example.

Example 1

Moisture contained in 2,3,3,3-tetrafluoropropene (HFO-1234yf) was removed by the following method. The method is described on the basis of the flow diagram shown in FIG. 1.

Using a water absorption column T11 (height: 3 m, inner diameter: 12 cm), HFO-1234yf with a moisture content of 2,000 weight ppm was continuously supplied from the bottom portion of the column at a rate of 13.8 kg/hr (S11). Meanwhile, an aqueous solution of lithium chloride with a concentration of 42 wt. % was supplied from the top portion of the column and sprayed into the column (S13). The pressure to supply HFO-1234yf into the column was 0.05 MPaG, and the column top temperature was 25° C.

HFO-1234yf supplied from the bottom portion was extracted from the top portion and sent to the subsequent step (S12). This operation allowed sufficient contact of HFO-1234yf contaminated with moisture supplied from the bottom portion with the aqueous solution of lithium chloride. Consequently, HFO-1234yf with a lower moisture content was obtained from the top portion.

On the other hand, the aqueous solution of lithium chloride supplied from the top portion was extracted from the bottom portion and circulated to the top portion (S13). A part of the extracted aqueous solution of lithium chloride was transferred to a dehydration tank V11 for thermal vacuum dehydration. The water resulting from dehydration was discharged (S15), and the aqueous solution of lithium chloride with a lower moisture content was placed in the lower part of the water absorption column T11 (S14). The concentration of the circulating aqueous solution of lithium chloride was thereby maintained constant.

Table 1 shows the component composition in each step.

TABLE 1

| | Stream | | | | |
|---|---|---|---|---|---|
| | S11 | S12 | S13 | S14 | S15 |
| | | | Flow rate (kg/hr) | | |
| HFO-1234yf | 13.8 | 13.8 | | | |
| Water | 0.0276 | 0.0055 | 10.2 | 0.28 | 0.0221 |
| LiCl | | | 7.4 | 0.22 | |
| Moisture content in gas (weight unit) | 2,000 ppm | 400 ppm | | | |
| Concentration of LiCl aqueous solution (weight unit) | | | 42 wt % | 44 wt % | |

As is obvious from these results, the above-described method can continuously and efficiently reduce the moisture content of HFO-1234yf.

The invention claimed is:

1. A method for removing moisture from hydrofluoroolefin compounds, the method comprising bringing a hydrofluoroolefin compound contaminated with moisture into contact with an aqueous solution containing a metal salt.

2. The method according to claim 1, wherein the hydrofluoroolefin compound is 2,3,3,3-tetrafluoropropene.

3. The method according to claim 1, wherein the metal salt is at least one member selected from the group consisting of lithium chloride, calcium chloride, magnesium chloride, and lithium bromide.

4. The method according to claim 3, wherein the metal salt is lithium chloride.

5. The method according to claim 1, wherein the aqueous solution containing a metal salt has a concentration of 20 to 50 wt. %.

6. The method according to claim 1, comprising the steps of reducing the moisture content of the metal salt-containing aqueous solution used in the method according to claim 1, and then reusing the aqueous solution to remove the moisture from the hydrofluoroolefin compound.

7. A method for removing moisture from hydrofluoroolefin compounds, the method comprising the steps of removing moisture from a hydrofluoroolefin compound by the method according to claim 1, and then bringing the thus-treated hydrofluoroolefin compound into contact with a water adsorbent.

* * * * *